United States Patent
Schilling et al.

(10) Patent No.: US 11,486,844 B2
(45) Date of Patent: Nov. 1, 2022

(54) RESISTIVE PARTICLE SENSOR

(71) Applicant: Robert Bosch GmbH, Stuttgart (DE)

(72) Inventors: Carolin Maria Schilling, Bad Schoenborn (DE); Enno Baars, Leonberg (DE); Karola Herweg, Stuttgart (DE); Mathias Klenk, Loechgau (DE)

(73) Assignee: Robert Bosch GmbH, Stuttgart (DE)

( * ) Notice: Subject to any disclaimer, the term of this patent is extended or adjusted under 35 U.S.C. 154(b) by 444 days.

(21) Appl. No.: 16/624,139

(22) PCT Filed: May 30, 2018

(86) PCT No.: PCT/EP2018/064147
§ 371 (c)(1),
(2) Date: Dec. 18, 2019

(87) PCT Pub. No.: WO2018/233994
PCT Pub. Date: Dec. 27, 2018

(65) Prior Publication Data
US 2020/0173947 A1    Jun. 4, 2020

(30) Foreign Application Priority Data
Jun. 23, 2017  (DE) .......................... 102017210625.5

(51) Int. Cl.
*G01N 27/12* (2006.01)
*G01K 7/16* (2006.01)
(Continued)

(52) U.S. Cl.
CPC ............ *G01N 27/124* (2013.01); *G01K 7/16* (2013.01); *G01K 13/02* (2013.01);
(Continued)

(58) Field of Classification Search
CPC ............ G01N 27/124; G01N 33/0036; G01N 15/0606; G01N 15/0656;
(Continued)

(56) References Cited

U.S. PATENT DOCUMENTS

| 4,903,110 A * | 2/1990 | Aono ...................... H01L 24/32 |
| | | 361/313 |
| 6,150,824 A * | 11/2000 | Mishra ................... G03G 15/75 |
| | | 399/73 |

(Continued)

FOREIGN PATENT DOCUMENTS

DE    102009028283 A1    2/2011

OTHER PUBLICATIONS

International Search Report for PCT/EP2018/064147, dated Aug. 20, 2018.

*Primary Examiner* — Nathaniel T Woodward
*Assistant Examiner* — Philip L Cotey
(74) *Attorney, Agent, or Firm* — Norton Rose Fulbright US LLP; Gerard A. Messina

(57) ABSTRACT

A resistive particle sensor is described for detecting soot in the exhaust gas of an internal combustion engine, including a sensor element having two strip conductors, which extend spaced apart in meanders in parallel to one another in an area of the sensor element that may be exposed to the exhaust gas, and a resistance strip conductor, the two strip conductors each being capacitively connected via capacitor elements to the resistance strip conductor.

5 Claims, 2 Drawing Sheets

(51) Int. Cl.
   *G01K 13/02*   (2021.01)
   *G01N 33/00*   (2006.01)
   *G01K 13/024*  (2021.01)
   *G01N 15/06*   (2006.01)
   *G01N 15/00*   (2006.01)

(52) U.S. Cl.
   CPC ....... *G01N 33/0036* (2013.01); *G01K 13/024* (2021.01); *G01K 2205/04* (2013.01); *G01N 15/0606* (2013.01); *G01N 15/0656* (2013.01); *G01N 2015/0046* (2013.01)

(58) Field of Classification Search
   CPC .. G01N 2015/0046; G01K 7/16; G01K 13/02; G01K 13/024; G01K 2205/04
   See application file for complete search history.

(56) References Cited

U.S. PATENT DOCUMENTS

| | | | | |
|---|---|---|---|---|
| 7,115,969 | B1* | 10/2006 | Patel | G01N 27/227 257/532 |
| 8,860,439 | B2* | 10/2014 | Kimata | G01N 15/0656 324/464 |
| 10,107,221 | B2* | 10/2018 | Wienand | F02D 41/1466 |
| 2008/0190173 | A1* | 8/2008 | Wienand | G01N 15/0656 422/68.1 |
| 2008/0241004 | A1* | 10/2008 | Jayne | F01N 3/0892 422/173 |
| 2009/0090622 | A1* | 4/2009 | Ripley | G01N 15/0656 204/412 |
| 2010/0123213 | A1* | 5/2010 | Chen | H01L 23/5225 257/532 |
| 2010/0180668 | A1* | 7/2010 | Kruse | G01N 15/0656 73/28.01 |
| 2011/0030451 | A1* | 2/2011 | Roesch | F02D 41/222 73/28.02 |
| 2011/0283773 | A1* | 11/2011 | Suzuki | G01N 15/0656 73/25.05 |
| 2012/0103059 | A1* | 5/2012 | Kimata | G01N 15/0656 29/25.42 |
| 2012/0119759 | A1* | 5/2012 | Nelson | G01N 35/00712 324/691 |
| 2012/0324981 | A1* | 12/2012 | Hedayat | G01N 15/0656 73/23.33 |
| 2013/0219990 | A1* | 8/2013 | Allmendinger | G01M 15/102 73/23.31 |
| 2014/0223887 | A1* | 8/2014 | Duault | G01N 1/2202 60/274 |
| 2015/0168285 | A1* | 6/2015 | Hedayat | G01M 15/102 73/23.33 |
| 2016/0017830 | A1* | 1/2016 | Wienand | G01N 15/06 73/23.31 |

* cited by examiner

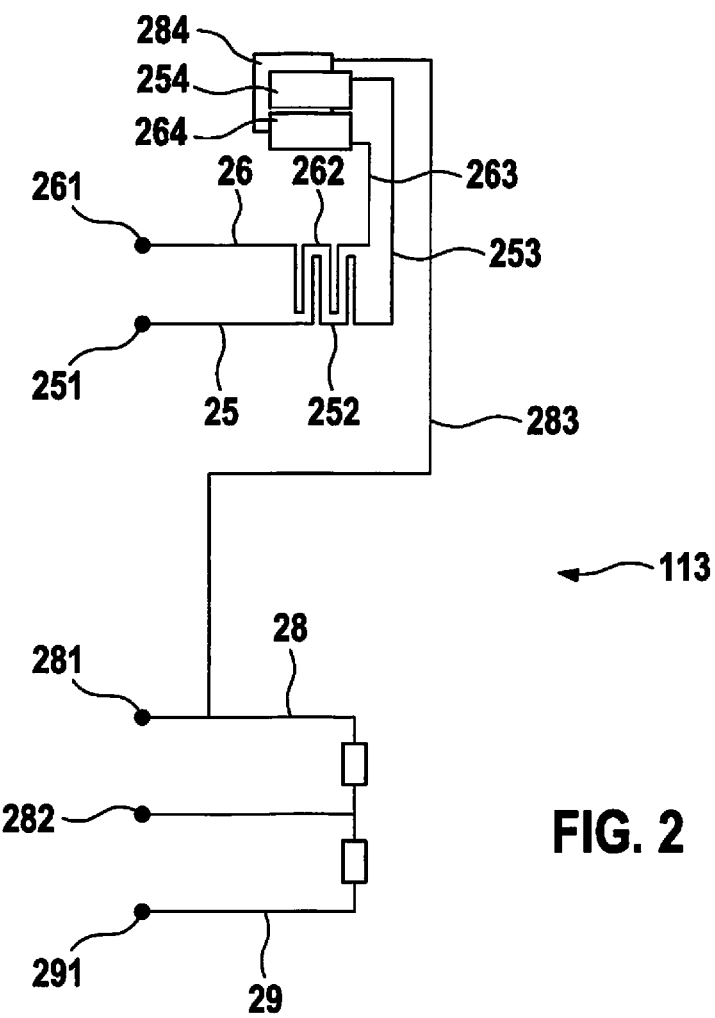
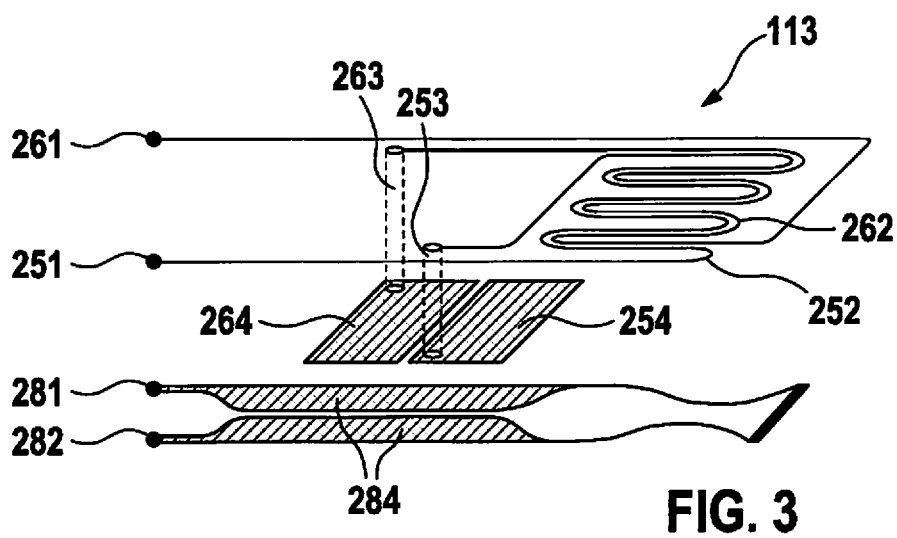

RESISTIVE PARTICLE SENSOR

BACKGROUND INFORMATION

A resistive particle sensor for detecting soot in the exhaust gas of an internal combustion engine, including a sensor element having two strip conductors extending spaced apart from one another in an area of the sensor element that may be exposed to an exhaust gas for the resistive detection of a particle quantity, is described in U.S. Patent Application Publication No. US 2012/0119759 A1.

A particle quantity is sensed with the aid of an electrical conductivity between the strip conductors.

To be able to differentiate the absence of soot in the exhaust gas from a deficient integrity of the particle sensor, a resistor which connects the strip conductors to one another is provided according to the related art.

This arrangement has the disadvantage that in the case of a particle quantity present between the strip conductors and a conductive connection between the strip conductors resulting therefrom, it is no longer possible to establish the integrity of the particle sensor unambiguously.

A resistive particle sensor for detecting soot in the exhaust gas of an internal combustion engine, including a sensor element having two strip conductors extending spaced apart from one another in an area of the sensor element that may be exposed to an exhaust gas for the resistive detection of a particle quantity, is also described in U.S. Pat. No. 8,860,439 B2. The strip conductors are each connected to "plate conductors" and extend spaced apart from one another in a straight line in the area of the sensor element that may be exposed to the exhaust gas. An interaction area between the strip conductors is therefore comparatively short. The sensitivity of the particle sensor is accordingly low.

A further resistive particle sensor is described in German Patent Application No. DE 101 33 384 A1 and includes comb-shaped strip conductors for resistively detecting a particle quantity and a plate capacitor, which is integrated into the sensor element and is electrically connected to the comb-shaped strip conductors.

SUMMARY

The particle sensor according to the present invention includes strip conductors which extend in meanders in parallel to one another in the sensitive area. An interaction area between the strip conductors is thus enlarged.

It is provided according to the present invention that the strip conductors each end in a capacitor element and are capacitively coupled to this capacitor element, which is electrically connected to a resistance strip conductor. In this way, the integrity of the particle sensor is ascertainable.

It is provided in particular that the strip conductors each end in a capacitor element and they are capacitively coupled to a capacitor element which is electrically connected to a resistance strip conductor.

In one preferred refinement, it is provided that the strip conductors are branch-free strip conductors, which each originate from a contact surface, which is situated outside the area that may be exposed to the exhaust gas, for contacting the sensor element, each lead from the contact surface to the area of the sensor element that may be exposed to the exhaust gas, extend in meanders therein, and subsequently lead to the capacitor elements, and the resistance strip conductor originates from a contact surface, which is situated outside the area that may be exposed to the exhaust gas, for contacting the sensor element, and leads to a further contact surface, which is situated outside the area that may be exposed to the exhaust gas, for contacting the sensor element, and the resistance strip conductor includes a capacitor element and/or is electrically connected to a capacitor element via a branch strip conductor.

The provision of the capacitor elements outside the area that may be exposed to the exhaust gas improves the service life of the particle sensor and its measurement accuracy over the service life.

Strip conductors are to be understood herein in particular as metallic structures, which in particular locally include a longitudinal extension and a transverse extension and a vertical extension in relation thereto and perpendicularly in relation to one another, the longitudinal extension in particular being substantially greater than the transverse extension and the vertical extension.

Strip conductors or strip conductor sections which extend in parallel to one another are to be understood within the scope of this application in particular as strip conductors or strip conductor sections, the longitudinal extension of which points locally in the same direction.

Strip conductors which extend in meanders are to be understood within the scope of this application in particular as strip conductors which include at least two, preferably at least three or at least four strip conductor sections in particular extending in parallel or essentially in parallel to one another, in particular turns of the strip conductors being situated in particular between adjacent strip conductor sections, which are in particular curves having an angle of 150° to 210°.

A capacitor element is to be understood herein in particular as an electrical conductor which, together with a further capacitor element and an electrical insulator situated between them, forms a capacitor. Capacitor elements may be formed flat, for example, and have an area of 25 to 200 mm$^2$.

A capacitor is to be understood herein in particular as a structure made of two electrical conductors (capacitor elements) insulated from one another, which are in particular different from the above-explained strip conductors. To qualify a capacitor in the meaning of the present invention, the two electrical conductors insulated from one another are in particular formed and spaced apart from one another in such a way that they are capable of storing 50 to 800 pC (picocoulomb) at a potential difference of 1 V. In other words: The value of the capacitance is in particular 50 to 800 pF (picofarad).

Capacitive couplings which are smaller and/or are not intentionally induced and/or desired with respect to the functionalities of the particle sensor, but rather are within the scope of capacitive couplings which necessarily occur in a resistive particle sensor, are not connected to a capacitor in the meaning of the present invention within the scope of the application.

It is furthermore particularly preferable if the value of the capacitance is not less than 100 pF and/or not greater than 400 pF.

A contact surface for contacting the sensor element is to be understood within the scope of this application in particular as areas, for example, end areas of strip conductors in which a transverse extension of the strip conductor is enlarged in particular.

It is provided in particular that the capacitor is constituted of metallic full-surface layered capacitor elements situated one over another and an insulation layer situated in between them. The value of the capacitance is particularly high in this case.

Alternatively, the metallic full-surface layered capacitor elements may be replaced in particular by metallic grids or by metallic linear structures. In this case, the ability to print over the capacitor elements is improved.

BRIEF DESCRIPTION OF THE DRAWINGS

FIG. 2 shows a first specific embodiment in schematic form.

FIG. 3 shows a second specific embodiment in schematic form.

DETAILED DESCRIPTION OF EXAMPLE EMBODIMENTS

Figure 1:
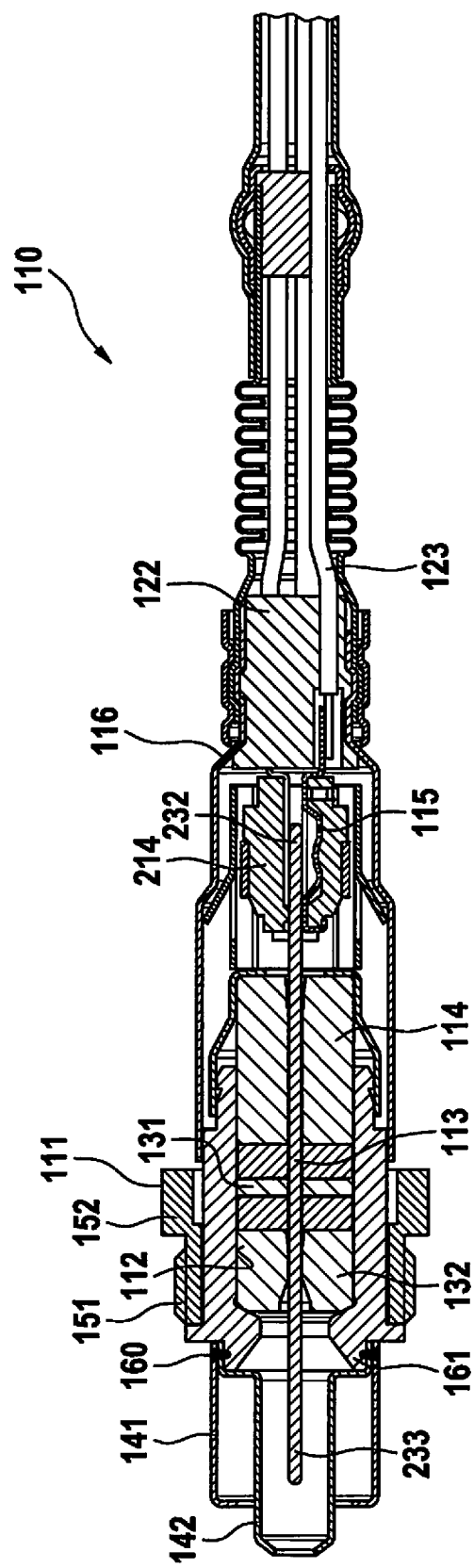
FIG. 1 shows an overview of a particle sensor according to the present invention.

FIG. 1 shows an overview of a particle sensor 110 according to the present invention in cross section along the longitudinal axis of particle sensor 110. This particle sensor 110 includes a metallic housing 111 having a through-hole 112, in which a ceramic sensor element 113 is fixed by a seal packing 131 and an exhaust-gas-side insulation sleeve 132 and a contact-side insulation sleeve 114. For example, 4 to 6 contact springs 115, which are in turn held in a contact holder 214, are pushed onto a contact-side end area of sensor element 232. On its side facing away from the exhaust gas, protective sleeve 116 is closed by a seal bushing 122, through which insulated conductors 123 electrically connected to contact springs 115 are guided.

Two coaxial protective tubes 141, 142 are fixed with the aid of a shared peripheral weld seam 160 on an exhaust-gas-side collar 161 of housing 111 on the side of metallic housing 111 facing toward the exhaust gas. Protective tubes 141, 142 include openings and cover and exhaust-gas-side end area of sensor element 233. This exhaust-gas-side end area of sensor element 233 is thus an area of sensor element 113 that may be exposed to the exhaust gas. In contrast, the contact-side end area of sensor element 232 is an area which may not be exposed to the exhaust gas in the meaning of the present invention.

Particle sensor 110 includes an external thread 151 and an external hexagon profile 152 for the installation in an exhaust system.

FIG. 2 schematically shows elements of sensor element 113 of the resistive particle sensor from FIG. 1. Strip conductors 25, 26 are branch-free and each originate from a contact surface 251, 261, which is situated outside the area that may be exposed to the exhaust gas, for contacting sensor element 113. From contact surface 251, 261, strip conductors 25, 26 lead to the area of sensor element 113 that may be exposed to the exhaust gas, where they extend in meanders 252, 262 in parallel to one another. Subsequently, strip conductors 25, 26 extend via supply line sections 253, 263 to capacitor elements 254, 264, which are situated flatly adjacent to one another in the example.

A resistance strip conductor 28, which is a resistance heater in the example, extends essentially in a layer plane below strip conductors 25, 26. A further resistance strip conductor 29, which is a temperature measurement resistance strip conductor in the example, extends essentially in a layer plane situated still further below.

Resistance strip conductor 28 and further resistance strip conductor 29 each include a contact surface 281, 291, which is situated outside the area that may be exposed to the exhaust gas, for contacting sensor element 113.

Resistance strip conductor 28 and further resistance strip conductor 29 lead to a further contact surface 282, which is situated outside the area that may be exposed to the exhaust gas and is shared in the example, for contacting sensor element 113. Shared contact surface 282 is connectable, for example, to a ground potential.

Resistance strip conductor 28 is connected via a branch line 283 to capacitor element 284, which is situated opposite to capacitor elements 254, 264 flatly and separated by an insulation layer (not shown) outside the area of sensor element 113 that may be exposed to the exhaust gas.

The two capacitor elements 254, 264 are formed over the entire surface and situated adjacent to one another. The two capacitor elements 254, 264 and the insulation layer form, together with capacitor element 284, a capacitance, whose value in the example may be a total of 150 pF (picofarad), 200 pF, or 300 pF.

A second specific embodiment is shown in FIG. 3. This differs from the specific embodiment shown in FIG. 2 in that capacitor element 284 of resistance strip conductor 28 is not formed separately, but rather is part of resistance strip conductor 28. In the example, capacitor element 284 is formed by widened strip conductors of resistance strip conductor 28, which are situated opposite to capacitor elements 254, 264 flatly and separated by an insulation layer (not shown). Capacitor elements 254, 264 are situated in the example in a different layer plane than the contact-side parts of strip conductors 25, 26. For this purpose, supply line sections 253, 254 are formed as a through-contact through a layer of sensor element 113.

Sensor element 113 may be manufactured, for example, in conventional thick-film technology.

What is claimed is:

1. A resistive particle sensor for detecting soot in the exhaust gas of an internal combustion engine, comprising:
a sensor element having two strip conductors, which extend spaced apart in meanders in parallel to one another in an area of the sensor element that may be exposed to the exhaust gas, and a resistance strip conductor, the two strip conductors each being capacitively connected via capacitor elements to the resistance strip conductor,
wherein the two strip conductors are branch-free strip conductors, which each originate from a contact surface, which is situated outside the area that may be exposed to the exhaust gas, for contacting the sensor element, each of the two strip conductors lead from the contact surface to the area of the sensor element that may be exposed to the exhaust gas, extend in meanders in the area of the sensor element that may be exposed to the exhaust gas, and subsequently lead to the capacitor elements, and the resistance strip conductor originates from a contact surface, which is situated outside the area that may be exposed to the exhaust gas, for contacting the sensor element and lead to a further contact surface, which is situated outside the area that may be exposed to the exhaust gas, for contacting the sensor element and the resistance strip conductor includes a capacitor element and/or is electrically connected to a capacitor element via a branch line.

2. The resistive particle sensor as recited in claim 1, wherein the capacitor elements are full-surface layers, between which an insulation layer is situated.

3. The resistive particle sensor as recited in claim 1, wherein the capacitor elements are metallic grids and/or line structures, between which an insulation layer is situated.

4. The resistive particle sensor as recited in claim 1, wherein a value of the capacitive connection is 50 to 800 pF (picofarad).

5. The resistive particle sensor as recited in claim 1, wherein the resistance strip conductor is a resistance heater and/or a temperature measurement resistance strip conductor.

\* \* \* \* \*